United States Patent [19]

Ghajar et al.

[11] Patent Number: 4,821,716
[45] Date of Patent: Apr. 18, 1989

[54] METHOD AND APPARATUS FOR PERPENDICULAR PERFORATION OF THE CRANIUM

[75] Inventors: Jamshid B. G. Ghajar; Robert J. Hariri; Fathali G. Ghadjar, all of New York, N.Y.

[73] Assignee: Neurodynamics, Inc., New York, N.Y.

[21] Appl. No.: 93,426

[22] Filed: Sep. 4, 1987

[51] Int. Cl.$^4$ .................... A61B 17/16; A61B 19/00
[52] U.S. Cl. ..................... 128/303 B; 128/92 VD; 128/305.1; 128/310; 604/174
[58] Field of Search .......... 128/303 B, 92 VD, 305.1, 128/310; 604/174

[56] References Cited

U.S. PATENT DOCUMENTS 3,017,887 1/1962 Heyer.
3,073,310 1/1963 Mocarski.
4,360,028 11/1982 Barbier et al. .............. 128/303 B X

OTHER PUBLICATIONS

Ghajar, A Guide for Ventricular Catheter Placement, J. Neurosurg., 63: 985-986 (1985) and Instruction Manual for described device.
Cooper, The Neurosurgical Alleviation of Parkensonism, Chemopallidectomy, p. 83 (1956).
Kandall, A Trephine Needle for Vertebral Body Biopsy, the Lancet, Feb. 27, 1960, p. 474.

Primary Examiner—Michael H. Thaler
Attorney, Agent, or Firm—Pennie & Edmonds

[57] ABSTRACT

An apparatus and method for drilling an orifice in a human cranium at an angle of substantially 90° to a plane defined by a tangent to the surface of the cranium at the orifice. The apparatus comprises a first tubular guide for directing a drill at the proper angle, the first guide being supported upon the cranium by a plurality of leg members. The invention further comprises a hand-operated twist drill device, configured for insertion into the tubular guide. A second guide, of reduced diameter relative to the first tubular guide is insertable into the first guide upon completion of the burr hole to facilitate entry of a catheter into the ventricular portion of the patient's brain. The method of the invention comprises positioning the first drill guide upon the patient's cranium, inserting the twist drill therein so as to prepare a burr hole extending at an angle of substantially 90° to a plane tangential to the surface, replacing the drill with a catheter guide insertable within the drill guide and inserting a catheter through the second guide, through the burr hole and into a ventricular portion of the patient's brain.

19 Claims, 2 Drawing Sheets

FIG. 6
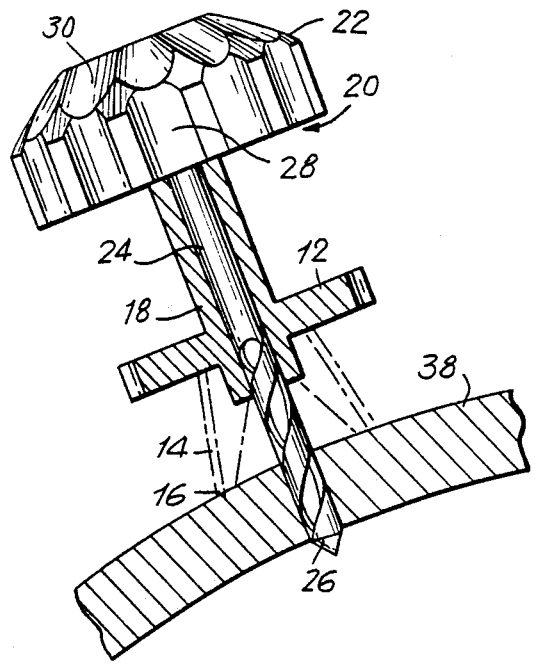
FIG. 7
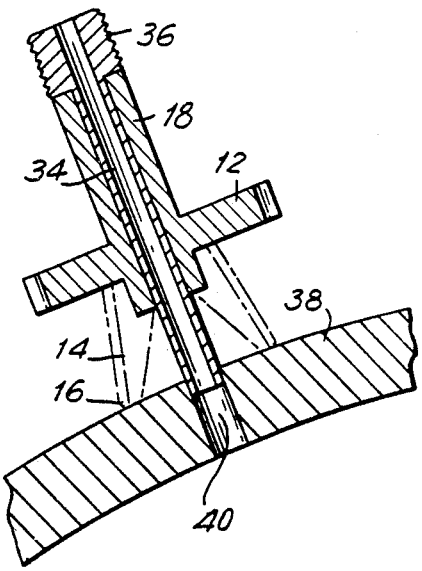
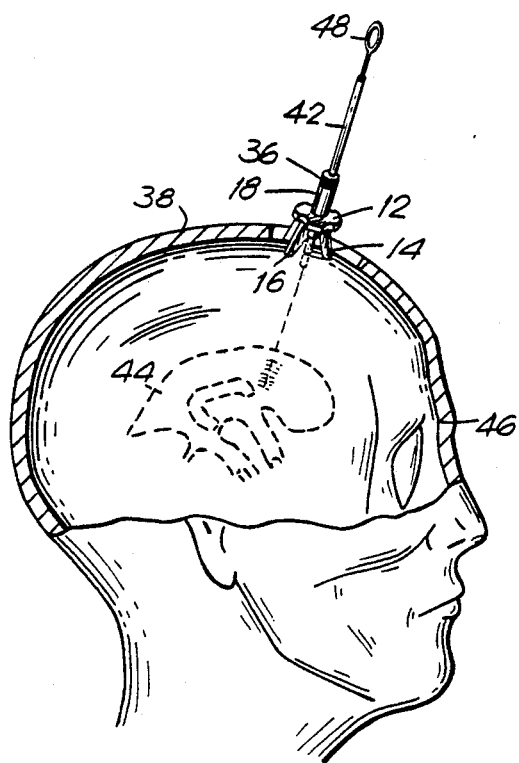
FIG. 8

METHOD AND APPARATUS FOR PERPENDICULAR PERFORATION OF THE CRANIUM

TECHNICAL FIELD

The invention relates to a method and apparatus for penetrating a human cranium at an angle of 90° to the surface. More particularly, the invention relates to a drilling device and a guide therefore to ensure that the perforation is oriented at the correct angle. An additional member may subsequently be inserted into the drill guide to facilitate the correct positioning of a catheter device within a ventricular portion of the patient's brain.

BACKGROUND OF THE INVENTION

The four ventricles of the human brain are interconnected cavities that produce and circulate cerebral-spinal fluid (CSF). Procedures involving ventriculostomy, i.e., placement of a catheter into the ventricular system of the brain, form a major part of a neurosurgeon's clinical practice. General areas of application of ventricular catheter placement include intracranial pressure monitoring (ICP), draining or shunting of CSF and the instillation of pharmacological therapeutic agents.

Intracranial pressure monitoring, i.e., a monitoring of ventricular pressure, is critical to the management of patients after severe head trauma, fulminant meningitis, Reyes' syndrome, encephalitis, stroke, cerebral hemorrhage, or subarachnoid hemorrhage producing stupor or coma. However, the ventricles are usually compressed after head trauma and thus technically difficult to cannulate for ICP monitoring. Accordingly, subarachnoid pressure monitoring, which is not as true a measure of cerebral pressure as intraventricular pressure monitoring, is generally used.

CSF drainage is essential for patients with congenital or acquired hydrocephalus. This procedure, which can only be performed with an intraventricular catheter, is a life-preserving step, because it can immediately reduce intracranial pressure. The ventricular catheter used to drain cerebral-spinal fluid is connected to a peripheral subcutaneous drainage system, i.e., to the peritoneal cavity or systemic circulation via the heart. In hydrocephalus, the ventricles are enlarged and are an easier target for cannulation. However, recent reports in neurosurgical literature indicate that suboptimal placement in dilated ventricles can subsequently produce catheter obstruction when the ventricles are decompressed and become smaller, thus emphasizing the need for accurate placement.

Catheter placement in cerebral ventricles is widely performed on patients with carcinomatous and fungal meningitis for the administration of well-known antineoplastic and antifungal chemotherapetuic agents, respectively. Invariably, the ventricles in these patients are small or normal sized and difficult to cannulate.

Standard procedures for ventricular catherization are disclosed in the textbook literature. See, for example, Neurosurgery, edited by Robert H. Wilkins and Setti S. Rengachary, Section A, Chapter 13, Techniques of Ventricular Puncture (McGraw Hill 1984).

The most frequently chosen site for ventricular catheterization is the coronal region. In most cases, a catheter is inserted in the anterior horn of the lateral ventricle through an orifice or burr hole drilled just anterior to the coronal suture in the midpupillary line of the cranium, i.e., in the frontal bone over the ventricle. This is known in the field as Kocher's point. The burr hole, only slightly larger than the diameter of the selected catheter to insure a snug fit and provide a seal against CSF leakage, is placed approximately 1 cm. anterior to the coronal suture, approximately 10 to 12 cm. above the nasion, and approximately 2 to 3 cm. from the midline over the nondominant hemisphere. After the burr hole is made, the dura and underlying pia-arachnoid are opened and coagulated, for example, with a fine-tipped blade, after cauterizing the dural surface.

The lateral ventricles of the human brain form an arc parallel to the arc of the cranium, i.e., the contour of the lateral ventricles parallels the arc of the surface of the skull. Thus, a catheter guided perpendicular to the cranial surface at the point of entry into the cranium will enter the ventricular system. Specifically, any line penetrating a burr hole in the surface of the skull at a 90° angle also bisects the lateral ventricle.

Various methods have been utilized in the prior art in an attempt to ensure the correct placement of a catheter device in the patient's cerebral ventrical. One such method involves the use of a pre-measured catheter having a stylet which may be introduced and directed freehand through the burr hole, approximately in the coronal plane, and angled towards the medial canthus of the ipsilateral eye, using external landmarks such as the inner canthus of the eye in the frontal plane and a point just in front of the external auditory meastus in the lateral plane as guided to placement. CSF should flow freely from the catheter tip at a depth of approximately 4 to 5 cm. from the interior cranial surface.

A distinctive "give", or release of opposition, can often be felt when the ventricle is penetrated. Pressure should be measured at this point, however, since an artificially low value will be obtained even if small amounts of fluid are lost. Then, after removal of the stylet from the catheter, advancement another 1 cm. or so should insure placement in the frontal horn at a depth of about 5 to 6 cm. from the external table of the skull, care being taken that CSF continues to flow.

Intraoperative fluoroscopy and air ventriculography, well known techniques in the art, have been used to confirm freehand catheter placement. While these procedures can be helpful in placing the catheter if the ventricles are small, they also add to the complexity of the overall procedure.

Aside from the cost and time constraints of such radiographic confirmation of catheter placement, many published reports of postoperative studies have revealed misplacement of catheter tips in cerebral matter or subarachnoid space. This misplacement results in increased neurological morbidity and the need for additional operation time. Moreover, multiple passes of the catheter into cerebral matter are quite common before the ventricles are properly penetrated. Finally, the anxiety a neurosurgeon experiences when trying to place a catheter by freehand into the ventricular system makes first pass success that much more difficult and further increases the risks involved in the procedure.

A more recently developed procedure to ensure correct catheter placement was disclosed and claimed by one of the present applicants in U.S. Pat. No. 4,613,324, issued Sept. 23, 1986. The disclosure of that patent is therefore specifically incorporated herein by reference. The apparatus comprises a guide assembly which, when positioned over an orifice drilled in the cranium above the anterior horn of the lateral ventricle, guides a catheter and obdurator through the orifice and into the lateral ventricle at an angle normal to an imaginary plane formed by a tangent to the cranium at the orifice.

The method of utilizing the claimed device comprises providing an orifice in the cranium just anterior to the coronal suture in a midpupillary line of the cranium and inserting a ventricular catheter containing an obdurator through the orifice towards a lateral ventricle, wherein the catheter containing the obdurator is guided through the orifice, by means of a novel guide assembly, at an angle normal to an imaginary plane formed by a tangent to the cranium at the orifice.

Although the procedures described above may be effective in positioning a catheter in a patient's lateral ventricle once a correctly aligned burr hole has been prepared for its passage, there is no art which the applicants are aware of which ensures that the initial perforation in the patient's cranium can be prepared and aligned so as to extend through the skull at an angle of substantially 90° to the surface thereof.

This orientation is required for proper placement of the catheter within the ventricular portion of the patient's brain since, if the burr hole deviates by more than about 7 degrees from the perpendicular to a plane tangent to the point on the cranium where the catheter is inserted, the catheter will be directed away from the ventricular region and into other areas of the organ not conducive to the intended purposes of the apparatus disclosed. Thus, aligning the burr hole in such a precise manner greatly simplifies the subsequent task of correctly aligning the catheter within the ventricular cavity.

The difficulty in obtaining such a precisely aligned burr hole has thus led to the search for a rapid, simple, inexpensive and accurate method and apparatus for perforating the patient's cranium at an angle of substantially 90° to the surface prior to the insertion of a catheter into the patient's cerebral ventricle.

SUMMARY OF THE INVENTION

An object of the present invention is to provide a method and apparatus for perforating a human cranium at an angle of substantially 90° to the surface thereof. This procedure facilitates the insertion of a catheter through the surface of the cranial bone and into the anterior horn of a lateral ventricle of the patient's brain, thus eliminating the problems, inaccuracies and risks associated with prior art methods.

Another object of the invention is to provide a method and apparatus for drilling through the cranial surface and inserting a catheter into the anterior horn of the lateral ventricle of the human brain which optimizes accurate and reproducible placement of the catheter.

Another object of the present invention is to provide a method and apparatus for accurately and reproducibly perforating the patient's skull and inserting a catheter through the cranial surface into the anterior horn of a lateral ventricle of the patient's brain in a manner which prevents insertion of the catheter into the cerebral matter or subarachnoid space.

A first embodiment of the present invention comprises an apparatus for drilling a hole in a human cranium at an angle of substantially 90° to a surface portion thereof. The apparatus comprises a guide member to direct and align a drill for cutting through the substrate at a proper angle, i.e., substantially 90° to a plane defined by a tangent to the substrate during the perforation thereof. The apparatus further comprises a drill which is insertable within an open bore portion of the drill guide member, which is operable to perforate the substrate. A catheter guide member, having an open bore portion with a diameter reduced in relation to the bore of the drill guide member, is insertable within the open bore portion of the drill guide member upon removal of the drill therefrom so as to effectively reduce the diameter of the drill guide member. Subsequently, fluid transport means, such as a catheter, may be inserted through the catheter guide member and thereafter into a ventricular portion of the patient's brain, in order to, for example, drain or shunt CSF therefrom or for the instillation of pharmacological therapeutic agents.

The apparatus may also include means for preventing penetration of said drilling means beyond a predetermined distance into said cranium.

A further object of the present invention is the correct placement of fluid transport means within this ventricular portion. Further, the fluid transport means described above may be a catheter which is adapted for the passage of fluid therethrough.

The drill guide member of the embodiment comprises a tube adapted to receive and guide the catheter therethrough and a support for the tube. This support is adapted to rest unsecured on the patient's cranium in surrounded spaced relation to the orifice. The support and the tube are related to each other and to the cranium so as to guide the catheter through the orifice and in a direction perpendicular to a plane defined by a tangent to the cranium at the orifice, independent of the orientation of the orifice. An insert within the tube, forming a catheter guide member, is adapted to be in guiding engagement with the catheter while the free end of the catheter is inserted into the ventricle of the brain. Advantageously, this catheter guide at least partially extends into the orifice which has been formed in the cranium.

The support may comprise a plurality of legs, each leg terminating in a free end. The free ends of these legs form a polygon defining a plane and the tube portion guides the catheter through the orifice in a direction perpendicular to this plane defined by the polygon and through the geometric center thereof. In a preferred embodiment, the legs are three in number and of equal length. Therefore, a polygon, i.e, a triangle formed by the free ends of these legs is an equilateral triangle. Further, the support may be connected to the tube through a connecting platform. Preferably, the guide as described above should be constructed of a rigid, non-deformable material such as as thermoplastic or stainless steel.

Another embodiment of the invention comprises a method for drilling an orifice in a human cranium at an angle at substantially 90° to a plane defined by a tangent to the cranium at the orifice and subsequently inserting a catheter into a ventricular portion of the brain within the cranium. The method iniitally comprises positioning a drill guide upon a portion of an outer surface of the patient's cranium such that an open tubular portion of the drill guide is oriented at an angle of substantially 90° to a plane defined by a tangent to the cranium at the orifice. The drill guide, as described above, comprises a tube and a support therefore.

The method further comprises drilling an orifice in the cranium by drilling means proximally anterior to a coronal suture in a midpupillary line of the cranium.

The orifice extends through the cranium at an angle of substantially 90° to a plane defined by a tangent to the cranium at the orifice. A catheter guide is thereafter inserted into the open tubular portion of the drill guide so as to render the diameter of the drill guide more consistent with that of a standard catheter. A catheter is subsequently guided through the the open portion of the catheter guide and thereafter through the orifice in a direction perpendicular to a plane defined by a tangent to the cranium at the orifice. Through the use of the present invention, therefore, the catheter accurately penetrates the ventricular portion of the brain upon the first insertion.

In a further embodiment of the invention, the method additionally comprises supporting the drill guide by a support comprising a plurality of legs. The legs are preferably three in number, each terminating in a free end. The free ends thus form a triangle defining a plane. An alternate embodiment of the invention comprises guiding the catheter through a catheter guide inserted within the drill guide and into the orifice and into the ventricular portion of the patient's brain in a direction perpendicular to the plane defined by the triangle formed by the legs of the support and through the geometric center thereof.

The drilling of the cranium can be performed manually, pneumatically, electrically or hydraulically by use of suitable drilling means. Also, the method includes the step of limiting the depth of penetration of the drilling means to a predetermined distance within the cranium by providing stop means on the drilling means for contacting the drilling guide means.

BRIEF DESCRIPTION OF THE DRAWINGS

The method and apparatus of the present invention will now be described with reference to the accompanying drawing figures, in which:

FIG. 6 is a sectional view illustrating the insertion of applicants' twist drill within the drill guide;

FIG. 7 is a sectional view illustrating the placement of applicants' catheter guide within the drill guide of the invention; and FIG. 8 is a view, partially in section, illustrating the usefulness of applicants' device for the insertion of a catheter into the lateral ventricle of a human brain.

DETAILED DESCRIPTION OF THE PREFERRED EMBODIMENTS

Figure 1:
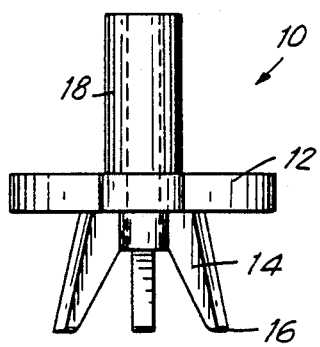
FIG. 1 is a side elevational view of applicants' drill guide.

Turning initially to FIG. 1 there is illustrated member 10 for controlling and directing a twist drill device (see FIGS. 3 and 4) during the formation of a burr hole through the cranium of a patient. The initial function of member 10 is to control the drill during the perforation of the cranium, thus preventing the bit from skipping on the bone or the scalp, especially at the start of the drilling procedure.

Member 10 may be seated, for example, directly upon the scalp of the patient, above an incision therein measuring on the order of from about 1-2 millimeters. Since, however, the skin of the scalp is loose and prone to movement relative to the cranial bone, the placement of member 10 in one position throughout the operative procesure serves to provide a means for readily locating the burr hole located beneath the incision. Since the diameter of the catheter placed within the burr hole ranges between only about 2-3 millimeters, the hole in the cranium need not be much greater in size, if at all, and it may therefore be difficult to relocate without the assistance of guide member 10.

Alternately, in the event a larger incision is made and member 10 is seated directly upon the surface of the skull, its legs spread apart the surrounding scalp tissue and prevent such tissue from being gathered or drawn to the drill bit during the operation, thus protecting the scalp from injury. Member 10 is thus preferably constructed of a rigid, non-deformable material such as a rigid engineering plastic or a metal such as stainless steel in order to fulfill these functions. The entire apparatus may be manufactured inexpensively from a plastic material, as a disposable assembly, thus reducing the cost of the assembly and assuring a sharp, sterilized drilling device for each operation. The availability of such a pre-sharpened, sterilized drilling device also serves to reduce the time required to complete each operation.

Figure 2:
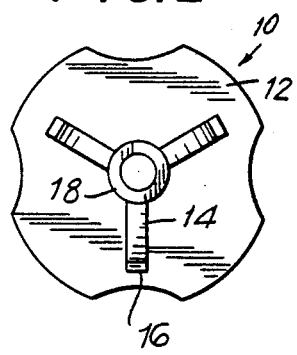
FIG. 2 is a lower plan view of a base portion of applicants' drill guide.

As shown in FIGS. 1 and 2, member 10 further comprises platform 12. Extending from platform 12 in a diverging manner are three legs 14, which terminate in free ends 16. Free ends 16 of legs 14 define a triangle lying within a defined plane.

Member 10 further includes guide means for guiding the drill in a direction perpendicular to the plane defined by the triangle formed by legs 14 and through the geometric center thereof. The guide means comprises a tubular member 18 extending through platform 12 in a direction perpendicular to the triangular plane described above.

Tubular member 18 is hollow, defining a central lumen to permit the passage therethrough of a drilling device (described below). The diameter of this lumen is not critical but it must, at a minimum, be sufficient to permit the passage of the drill. When member 10 is placed on the patient's cranium with the free ends 16 of legs 14 resting thereupon, the plane of the triangle defined by free ends 16 coincides with a plane tangent to the cranial surface directly below tubular member 18.

Accordingly, member 10 directs the drilling device perpendicular to this tangential plane, ensuring the production of a burr hole through the cranial bone at an angle of 90 degrees to the surface of a plane tangent to the cranium. This alignment assures that a ventricular catheter, inserted into the brain in a direction perpendicular to the curvature of the cranium, will not deviate from a preferred course due to a misaligned skull hole. As noted above, if the orientation of the bore hole deviates by more than about 7 degrees from the prependicular to a plane tangent to the cranium at the point of insertion of the catheter, the catheter is much more likely to be misaligned and to miss the ventricular portions of the brain entirely.

Preferably, legs 14 of member 10 are of equal length, equidistantly spaced and symmetrically disposed relative to each other, whereby the free ends 16 define an equilateral triangle. Guide means 18 directs the drill perpendicular to the plane defined by this equilateral triangle at the geometric center thereof and hence, perpendicular to the tangent plane upon the surface of the patient's cranium.

It is, however, nevertheless possible to practice the invention with a member 10 having an asymmetric arrangement of legs 14, as long as the guide means, i.e., tubular member 18, of member 10 extends perpendicularly to the plane defined by the free ends 16 of legs 14 and the member 10 is placed on the cranial surface such that this plane coincides with a plane tangent to the cranium at the orifice.

Similarly, the invention may be practiced with a guide member 10 having more than three legs, as long as the above-described directional criteria are maintained. Additionally, while tubular member 18 is illustrated as being cylindrical in shape, any shape which allows an unencumbered passage of the drill therethrough may be employed.

FIG. 2 is a bottom plan view of member 10, further illustrating the perpendicular intersection of guide means 18 with the plane of the triangle defined by free ends 16 of legs 14.

While the preferred embodiment of member 10, as described above, includes platform 12 for connecting legs 14 to tubular member 18, platform 12 is not an essential element of member 10. Thus, legs 14 may be connected directly to tubular member 18 as long as tubular member 18 guides the drill in a direction perpendicular to the plane of the triangle formed by the free ends 16 of legs 14 and through the geometric center of this triangle.

The height of member 10 and the distance between free ends 16 of legs 14 may be varied, as long as the following principles are observed. First, the base portion of member 10 must preferably form an equilateral triangle defined by free ends 16 of legs 14. Secondly, a line passing through the central lumen of tubular member 18 must be normal to the plane of the triangle thus defined and must pass through the geometric center thereof. Furthermore, the internal diameter of the central lumen may be varied, as long as the lumen is constructed of a sufficient width to accept applicants' twist drill.

Preferably, the distance between free ends 16 of legs 14 ranges from about 1 cm to about 6 cm. The lower limit is established based on the smallest burr hole or orifice necessary for passing a catheter therethrough. These catheters may range from about 2–3 millimeters in diameter. The upper limit is established based on the change in skull curvature which occurs when the midline of the skull is crossed.

Specifically, since the orifice or burr hole is drilled generally from about 2 cm to about 3 cm from the midline, an upper limit of about 6 cm is preferred so that one or more legs do not rest on the skull at a point beyond the midline where the skull curvature has changed. This would place member 10 at such an angle that tubular member 18 would not be directed normal to the imaginary plane defined by a tangent to the orifice at the point of entry.

The specific height of member 10 is also not a critical parameter. A preferred height range is about 2 cm to about 10 cm. The lower limit is established on the basis of the usual length of a catheter (15 cm) minus the standard intracranial distance to the ventricle (5 cm).

Although the member 10 of the present invention has been illustrated with three legs 14, this is not a critical limitation. For example, member 10 of the present invention may be constructed with four legs. In such an embodiment, the free ends of each of the four legs define the corners of a polygon such as a square or rectangle and the axis of tubular member 18 passes through the geometric center of the square or rectangle, wherein the axis is normal to the plane thereof.

Figure 3:
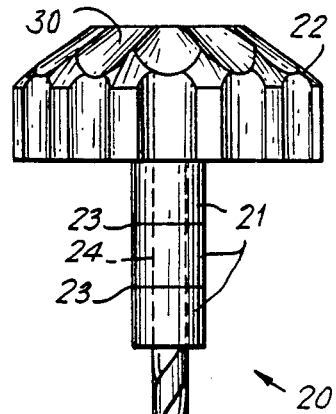
FIG. 3 is a side elevational view of applicants' twist drill and handle assembly.

Turning now to FIG. 3 there is illustrated applicants' twist drill device 20 comprising handle 22, shaft 24 and drill bit 26. Drill 20 must be constructed of a material such as steel having a high degree of structural strength, so as to facilitate the penetration of the patient's cranium thereby. However, handle 22 may be formed of a different material, such as a rigid plastic, since it serves as a grip for drill 20 and does not penetrate the bony surface of the skull. Although applicants' device is depicted as a hand-operated twist device, various other drills, such as pneumatic drilling devices may be utilized and the invention should thus not be limited to the embodiment illustrated herein.

Drill 20 is further provided with a number, i.e., preferably three, of spacer rings 21 which are preferably "C"-shaped, but which may be circular or of some other alternate shape and whose open portion engages shaft 24. The purpose of spacer rings 21 is to prevent the penetration of drill 20 past a predetermined distance into the patient's cranium. As drill 20 penetrates the cranium at a certain depth, a lower surface of lower ring 21 contacts the upper portion of tubular member 18 and thus prevents further passage of drill 20 therethrough until at least one ring member 21 is removed. Rings 21 may preferably be fabricated of plastic and each is approximately 1 cm in thickness. They may either be constructed as separate units, or alternately, they may be produced as a single unit having a perforated portion 23 at various positions along the width, e.g., preferably 1 cm apart. This permits 1 cm thicknesses of ring 21 to be snapped off and removed from drill shaft 24, thus permitting shaft 24 of drill 20 to travel deeper into member 10 in the event that the patient's cranium is thicker than originally anticipated.

In the event, therefore, that a patient is to undergo a ventriculostomy procedure, guide 10 is seated upon the patient's scalp over a small incision made therein or, alternately, directly over the skull itself. Shaft 24 of drill 20 is then inserted into tubular member 18 of member 10 to a point where drill bit 26 contacts the patient's cranium. A perforation is subsequently made through the cranial bone by the surgeon pressing on and turning the handle of drill 20 with one hand while holding member 10 with the other hand.

As noted above, in the event that member 10 is removed from the surface of the cranium prior to the completion of the procedure, it would be difficult if not impossible to relocate the site of the burr hole under the small, i.e., 1 cm, incision customarily made in the scalp for this purpose. The device thus produces a burr hole at an angle of substantially 90° to a plane defined by a tangent to the surface of the cranium, thus assuring that a catheter which is subsequently to be inserted into the ventricular portion of the brain, perpendicular to the curvature of the cranium, will not deviate due to a misaligned skull hole.

Figure 4:
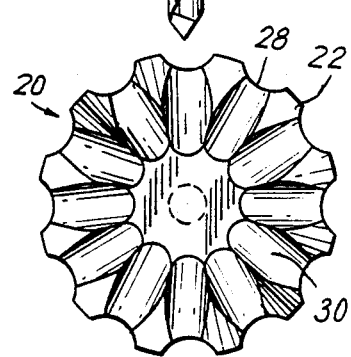
FIG. 4 is a top plan view of applicants' twist drill handle.

FIG. 4 clearly illustrates the molded handle portion 22 of drill 20. The shaft portion 24 of drill 20 is attached to handle 22 by fastening means such as, for example, a threaded screw, which passes through an aperture in the center of handle 22 and engages a hollow upper portion of shaft 24. Further, handle 22 is constructed with a series of peripheral grooves 28 located along the outer periphery thereof. The purpose of grooves 28 is to provide a firm grip for the surgeon upon drill 20 to prevent slippage during the formation of a burr hole through the patient's cranium. A second set of grooves 30 is circumferentially located along an inner surface of handle 22 to further assist the surgeon in obtaining a secure grip upon drill 20 during the operation.

Figure 5:
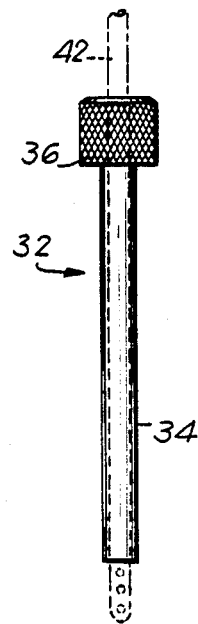
FIG. 5 is a side elevational view of applicants' catheter guide, configured for insertion into the drill guide of the invention.

Once the bore hole has been prepared at an angle of substantially 90° to a plane tangent to the surface of the patient's cranium, drill 20 is removed from member 10 and catheter guide 32 (shown in FIG. 5) is inserted into tubular member 18. Guide 32 comprises a tubular member 34 with a lumen having a reduced diameter relative to tubular member 18 of guide 10. Guide 32 is further provided with a relatively wider top portion which serves as a stop 36 to position catheter guide 32 within member 10.

FIG. 6 depicts the operation of drill 20 within member 10. As noted above, drill 20 is inserted into tubular member 18 of member 10 until the point of drill bit 26 contacts cranium 38. Handle 22 is then grasped by the surgeon and rotated until drill bit 26 passes completely through cranium 38. Thereafter, the underlying dura and pia-arachnoid tissue may be pierced with the assistance of a needle inserted therethrough and thus prepared for the passage of a catheter.

Once the formation of burr hole 40 is completed, catheter guide 32 is inserted within the tubular member 18 of member 10, as shown in FIG. 7. As noted previously, the purpose of guide 32 is to reduce the lumen diameter of drill member 10 to a size more correlative with that of a catheter 42 to be inserted therethrough.

In an alternate, preferred embodiment of the invention, guide 32 may be constructed having a length sufficient to pass completely through member 10 and at least partially into burr hole 40. In the event, therefore, that the guide assembly is moved or is removed from the patient's cranium for any reason, burr hole 40 may be easily relocated by positioning member 10 over the incision in the patient's scalp and simply rotating the assembly until guide 32 slips into burr hole 40 for the convenient passage of catheter 42 therethrough into the ventricular portion of the brain.

FIG. 8 illustrates the insertion of catheter 42 wherein a burr hole 40 is drilled on the right or left side of a patient's cranium 38 in the midpupillary line. The orifice 40 is located above the anterior horn of lateral ventricle 44, approximately 10 cm. posterior to the nasion and approximately 3 cm. lateral to midline 46 of the cranium. After drilling of the orifice 40 is complete, the dura and underlying pia-arachnoid (not shown) are cut and coagulated, in a manner well known in the art.

A catheter 42 containing a rigid obdurator 48 is then accurately guided through the orifice 40 and dural opening into ventricle 44 by the guide assembly 10, 32, which is placed and rests on the skull over the orifice 40. Any well known catheter 42 and obdurator 48, such as the commercially-available Codman Accu-flo ventricular catheter and obdurator, made by Codman and Shurtleff, Inc., may be used in the present invention.

Accordingly, guide assembly 10, 32 will direct catheter 42 perpendicular to the tangent plane described above at the center of burr hole 40, ensuring the correct positioning of catheter 42 within the ventricular system of the patient's brain. Subsequent to such entry, the obdurator 48 is withdrawn, leaving catheter 42 in place to perform its intended function.

The method and apparatus of the present invention thus insures optimal ventricular catheter placement. The invention may thus be used in any situation requiring placement of a catheter in the ventricular system, e.g., intracranial pressure monitoring, drainage or shunting of cerebral-spinal fluid and the introduction of pharmacologic therapeutic agents. Moreover, the present invention is so anatomically consistent that it can be employed as a reference point for biopsy of brain lesions.

The present invention thus eliminates the complications often encountered due to the anxiety ordinarily experienced by neurosurgeons regarding the insertion of a catheter. Patient care is thus improved by eliminating these complications and the associated morbidity. A reduction in the cost to the patient is also achieved by eliminating the need for intraoperative radiographic monitoring and by decreasing operating room time.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

We claim:

1. An apparatus for drilling an orifice in a human cranium at an angle of substantially 90° to a plane defined by a tangent to a surface portion thereof, said apparatus comprising:
    (a) hand-held means for guiding drill means upon said cranium at an angle of substantially 90° to a plane defined by a tangent to said cranium during the perforation thereof, said drill guiding means adapted for resting unsecured upon any portion of said cranium;
    (b) means insertable within an open bore portion of said drill guiding means for drilling an orifice in said cranium;
    (c) means for guiding a fluid transport member having a bore portion with a reduced diameter in relation to said bore of said drill guiding means and insertable within said open bore portion of said drill guiding means upon removal of said drilling means so as to effectively reduce the diameter of said open portion; and
    (d) means for preventing penetration of said drilling means beyond a predetermined distance into said cranium.

2. The apparatus of claim 1, further comprising a fluid transport member insertable through said fluid transport guiding means and said orifice and into a ventricle of said cranium.

3. The apparatus of claim 2, wherein said fluid transport means is catheter means.

4. The apparatus of claim 3, wherein said first guide means comprises:
    (a) tubular means adapted to receive and guide said catheter means therethrough; and
    (b) support means for said tubular means, said support means being adapted to rest unsecured on said human cranium in surrounding spaced relation to said orifice,
said support means and said tubular means being related to each other and to said cranium so as to guide said drill means through said tubular means and in a direction perpendicular to a plane defined by a tangent to the cranium at said orifice.

5. The apparatus of claim 4, wherein said support means comprises a plurality of legs.

6. The apparatus of claim 5 wherein each of said plurality of legs terminates in a free end, said free ends forming a polygon defining a plane, said tubular means guiding said drill means through said tubular means in a direction perpendicular to the plane defined by said polygon and through the geometric center of said polygon.

7. The apparatus of claim 6 wherein said support means comprises three legs of equal length and wherein an equilateral triangle is formed by said free ends of said legs.

8. The apparatus of claim 4, wherein said support means is connected to said tubular means through a connecting platform.

9. The apparatus of claim 4, wherein said guide means is made of a rigid plastic or stainless steel.

10. The apparatus of claim 1 wherein said fluid transport guiding member is adapted to at least partially extend into said orifice in said cranium.

11. The apparatus of claim 1 wherein said means for preventing penetration of said drilling means beyond a predetermined distance into said cranium comprises a plurality of detachable spacer ring members, each said ring member adapted for engaging a shaft portion of said drilling means such that a lower surface of a lower one of said ring members contacts said drill guiding means as said drilling means is rotated to prevent further passage of said drilling means therethrough.

12. A hand-held apparatus for drilling an orifice in a human cranium at an angle of substantially 90° to a plane defined by a tangent to said cranium at said orifice and subsequently accurately and reproducibly inserting a catheter through said orifice and into a ventricle of a human brain, said apparatus comprising:
(a) first tubular means for receiving and guiding drilling means;
(b) means for supporting said first tubular means, said support means being adapted to rest unsecured on any portion of said human cranium in surrounding spaced relation to said orifice;
(c) means for drilling an orifice through said cranium configured for insertion within said first tubular means, said drilling means having means for preventing penetration thereby beyond a predetermined distanced into said cranium, said orifice extending at an angle of substantially 90° to a plane defined by a tangent to said cranium at said orifice; and
(d) second tubular means for guiding catheter means into said cranium, comprising an internal open bore portion having a reduced diameter relative to a corresponding open bore portion of said first tubular means but of a sufficient size to permit the passage of said catheter means therethrough, said second tubular means being adapted for insertion within said first tubular means to reduce the effective diameter of said internal bore portion of said first tubular means; said support means and said second tubular means being related to each other and to said cranium, upon the insertion of said second tubular means into said open bore portion of said first tubular means, so as to guide said catheter through said orifice in a direction perpendicular to a plane defined by a tangent to said cranium at said orifice, independent of the orientation of the orifice, and said second tubular means adapted to be in guiding engagement with said catheter while the free end of said catheter is inserted into said human brain.

13. The apparatus of claim 12 wherein said fluid transport guiding member at least partially extends into said orifice of said cranium.

14. The apparatus of claim 12 wherein said means for preventing penetration of said drilling means beyond a predetermined distance into said cranium comprises a plurality of detachable spacer ring members, each said ring member adapted for engaging a shaft portion of said drilling means such that a lower surface of a lower one of said ring members contacts said drill guiding means as said drilling means is rotated to prevent further passage of said drilling means therethrough.

15. A method for drilling an orifice in a human cranium at an angle of substantially 90° to a plane defined by a tangent to said cranium at said orifice and subsequently inserting catheter means into a ventricular portion of a human brain within said cranium, said method comprising:
(a) positioning hand-held drilling guide means upon any portion of an outer surface of said cranium such that an open tubular portion of said drilling guide means is oriented at an angle of substantially 90° to a plane defined by a tangent to said cranium at said surface portion; said drilling guide means comprising tubular means and support means therefore, said support means being adapted to rest unsecured on said cranium in spaced relation to said orifice;
(b) drilling an orifice in said cranium by drilling means proximally anterior to a coronal suture thereof in a midpupillary line of said cranium, said drilling means having means for preventing penetration thereby beyond a predetermined distance into said cranium, said orifice extending through said cranium at an angle of substantially 90° to a plane defined by a tangent to said cranium at said orifice;
(c) inserting a catheter guide means into said open tubular portion of said drilling guide means to as to reduce the diameter of said drilling guide means to a measurement more consistent with that of said catheter means; and
(d) guiding said catheter means through said catheter guide means and thereafter through said orifice in a direction perpendicular to a plane defined by a tangent to the cranium at the orifice, whereby the catheter accurately penetrates the ventricular portion of said brain upon the first insertion.

16. The method of claim 15 further comprising supporting said tubular means through a support means comprising a plurality of legs.

17. The method of claim 15 wherein said tubular means is supported through a support means comprising a plurality of legs terminating in free ends, said free ends forming a polygon defining a plane, said method comprising guiding said catheter through said catheter guide means and into said orifice and ventricle in a direction perpendicular to the plane defined by said polygon and through the geometric center of said polygon.

18. The method of claim 15 wherein the drilling of said cranium is performed manually, pneumatically, electrically, or hydraulically.

19. The method of claim 15 wherein said drilling means is prevented from penetrating said cranium beyond a predetermined distance by providing stop means on said drilling means for contacting said drilling guide means to prevent further penetration of said cranium by said drilling means.

* * * * *